(12) United States Patent
Kawazoe et al.

(10) Patent No.: US 6,725,708 B2
(45) Date of Patent: Apr. 27, 2004

(54) IMPRESSION FORMING MECHANISM AND METHOD, AND HARDNESS TESTING APPARATUS AND METHOD

(75) Inventors: Masaru Kawazoe, Kanagawa (JP); Mituru Oda, Kanagawa (JP); Tomoharu Yamada, Kanagawa (JP)

(73) Assignee: Akashi Corporation, Kanagawa (JP)

( * ) Notice: Subject to any disclaimer, the term of this patent is extended or adjusted under 35 U.S.C. 154(b) by 0 days.

(21) Appl. No.: 10/242,352

(22) Filed: Sep. 13, 2002

(65) Prior Publication Data

US 2004/0050149 A1 Mar. 18, 2004

(51) Int. Cl.[7] .................................................. G01N 3/48
(52) U.S. Cl. ............................................................ 73/81
(58) Field of Search ........................................ 73/78–85

(56) References Cited

U.S. PATENT DOCUMENTS 4,118,975 A * 10/1978 Iwasaki ............................ 73/81
6,336,359 B1    1/2002 Kawazoe et al.
6,484,570 B2   11/2002 Kawazoe et al.

FOREIGN PATENT DOCUMENTS

JP  B2-57-40965   8/1982
JP  B2-58-19218   4/1983

* cited by examiner

Primary Examiner—Robert Raevis
(74) Attorney, Agent, or Firm—Oliff & Berridge, PLC

(57) ABSTRACT

A hardness testing apparatus comprises a sample table mounting a sample thereon, a loading arm having an indentor at its free end, a loading arm operation controlling unit, an electromagnetic brake. When the same is elevated and brought into contact with the indentor, the loading arm is moved upwardly. The loading arm operation controlling unit calculates a predetermined force to be applied to the sample in response to a displacement from a reference position of the loading arm when and after the sample is brought into contact with the indentor. The loading arm is moved upwardly such that a predetermined force calculated by the loading arm operating controlling unit is applied to the sample. The electromagnetic brake controls an elevating operation of the sample table. A direction of a current supplied to the electromagnetic brake is inverted at a predetermined timing.

10 Claims, 13 Drawing Sheets

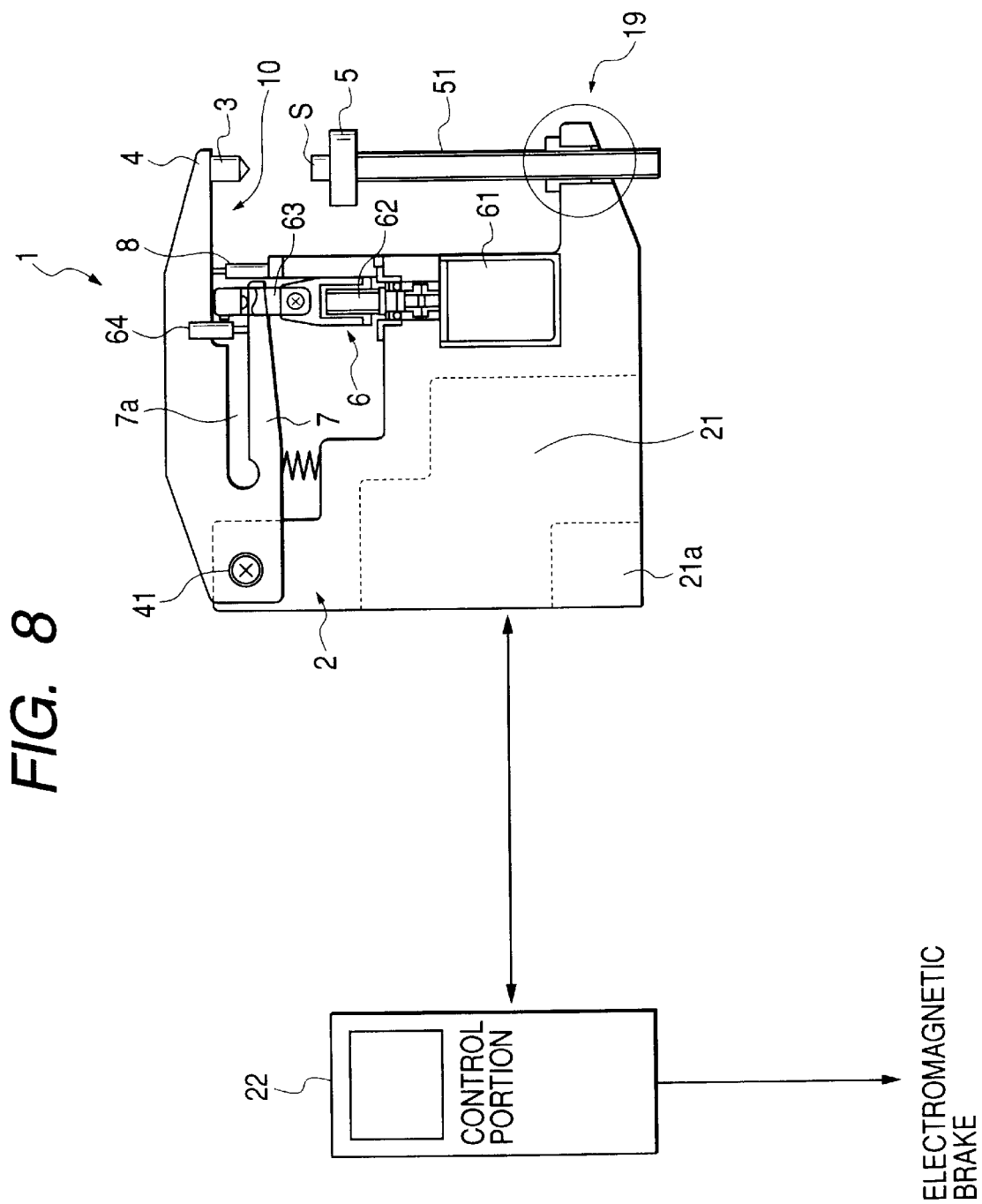

IMPRESSION FORMING MECHANISM AND METHOD, AND HARDNESS TESTING APPARATUS AND METHOD

BACKGROUND OF THE INVENTION

1. Field of the Invention

The present invention relates to an impression forming mechanism and an impression forming method which are employed in a testing apparatus that evaluates a material characteristics of a sample by applying a force to a surface of the sample with an indentor in order to from an impression thereon, and a hardness testing apparatus comprising the impression forming mechanism and method. The present invention also relates to a hardness testing apparatus and a hardness testing method, having an electromagnetic brake.

2. Description of the Related Art

In the related art, a hardness testing apparatus is known as a testing apparatus that evaluates the material characteristics of a sample based on an impression formed by applying a force (or load) to a surface of the sample with an indentor.

As a force applying mechanism in the hardness testing apparatus in the related art, for example, a mechanism shown in FIG. 13 is known.

A hardness testing apparatus 100 as shown in FIG. 13 is the so-called Rockwell type hardness testing machine. The hardness testing apparatus 100 has an impression forming mechanism 110 comprising weights 101, a loading arm 102, a cam 103, a force shaft 104, an indentor shaft 105, an indentor 106, etc., and a sample table 107.

In the impression forming mechanism 110, the weights 101 having a predetermined weight are hung from an end of the loading arm 102. The end of the loading arm 102 moves down by the rotation of the cam 103, and then a predetermined force (or load) is applied to the force shaft 104. The force applied to the force shaft 104 is transmitted to the indentor 106 via the indentor shaft 105. Thus, an impression is formed on a sample mounted on the sample table 107, by a downward movement of the indentor 106.

In a force applying control by using the weights, which is employed typically in the above hardness testing apparatus 100, there is a problem that it cannot be confirmed whether the force having a set value is applied to the sample while an impression is formed on the surface of the sample.

Also, since the force is applied to the sample by using the weights, the force that exceeds a target force, i.e., the so-called overshoot, is generated unless a speed for applying the force to the sample is slowed down by a damper, or the like. There is also a problem that, even if the damper is employed, it is difficult to eliminate the small overshoot.

In order to overcome the problems, there is a method that the force is applied to the sample by executing electrically the force applying control. In the case of the electrical force applying control, the loading arm having a high rigidity is employed for the convenience of control.

Further, an electromagnetic brake is employed for stopping the sample table once when the sample is brought into contact with the indentor in order to apply a preliminary test force to the surface of the sample.

The electromagnetic brake uses an electromagnet that is arranged under the sample table, and if a predetermined force is applied to the indentor when the sample is brought into contact with the indentor, a current is passed through the electromagnet so that a brake is applied to an elevating operation of the sample table. With the electromagnetic brake, an operation of applying the force to the sample can be carried out precisely.

However, in the hardness testing apparatus having the loading arm with the high rigidity, an impact (stepwise force) is easily applied to the sample at an instant when the sample and the indentor are brought into contact with each other manually. In some cases, a force that excesses the preliminary test force is easily applied to the sample at an instant when the sample and the indentor are brought into contact with each other manually.

In such case, there is a problem that the hardness testing apparatus cannot be carried out preciously.

Further, for the sample table, a high mechanical strength and a high rigidity are required, and thus a magnetic substance such as iron, or the like is used as the material for the sample table. Accordingly, due to the use of the electromagnet of the electromagnetic brake, the sample table is magnetized and also the sample mounted on the sample table is magnetized.

Such magnetization is at the level that the measuring precision of the hardness testing apparatus is not influenced. However, in the test of the sample, such as a thin sample, a lightweight sample, or the like, which is easy to be attracted to the magnet, the sample is attracted to the electromagnet and pasted onto the sample table, whereby a replacing operation of the sample becomes troublesome.

SUMMARY OF THE INVENTION

The present invention has been made to overcome the above problems. In is a first object of the present invention is to provide an impression forming mechanism and an impression forming method and a hardness testing apparatus, having a loading arm with high rigidity, which can reduce an impact generated at an instant when an indentor and a sample are brought into contact with each other and also apply an preliminary test force to the sample easily and precisely.

Further, it is a second object of the present invention to provide a hardness testing apparatus and a hardness testing method, having an electromagnetic brake, which can test a thin sample, etc. effectively and also can test a sample, in which a problem is caused if the sample is magnetized.

In order to accomplish the first object above, the following means are adopted. According to a first aspect of the present invention, there is provided an impression forming mechanism for forming an impression on a surface of a sample with an indentor, comprising:

an impact reducing unit for controlling a movement of one of the sample and the indentor in a same direction as the other of the sample and the indentor when the sample comes close to the indentor and a distance between the sample and the indentor is within a predetermined distance.

According to the impression forming mechanism of the first aspect of the present invention, since the impact reducing unit is provided, the impulse that is applied to the sample by the indentor at an instant when the sample comes into contact with the indentor can be reduced. In other words, since the impact generated at an instant when the sample comes into contact with the indentor can be reduced, it is possible to overcome the problem such that the force exceeds a preliminary test force at an instant of contact.

In the impression forming mechanism of a second aspect of the present invention, according to the first aspect of the present invention, it is preferable that the impact reducing unit controls the movement of one of the sample and the indentor in a same direction as the other when the sample comes into contact with the indentor, the impact reducing unit including, a force controlling unit for calculating a predetermined force which is to be applied to the sample, in response to a displacement from a reference position of the indentor when the sample comes into contact with the indentor, and a moving unit for moving the indentor in a same direction as the sample such that the predetermined force calculated by the force controlling unit is applied to the sample.

According to the impression forming mechanism of the second aspect of the present invention, since the force controlling unit and the moving unit are provided, the force can be applied to the sample in response to the displacement from the reference position of the indentor. Thus, the operator who moves the sample manually can apply the predetermined force to the sample more appropriately by operating only the handle, etc. in the same manner as the related art.

In the impression forming mechanism of a third aspect of the present invention, according to the first or second aspect of the present invention, it is preferable that the impact reducing unit further includes a distance sensing unit for sensing the distance between the indentor and the sample, and the impact reducing unit controls the movement of one of the sample and the indentor in a same direction as the other at a predetermined speed when the sample comes close to the indentor.

According to the impression forming mechanism of the third aspect of the present invention, since the distance sensing unit is provided, the one of the sample and the indentor can be moved in the same direction as the other immediately before the sample is brought into contact with the indentor. Thus, the impact can be reduced further more at an instant when the sample comes into contact with the indentor.

Further, in order to accomplish the first object above, there is provided a hardness testing apparatus according to a fourth aspect of the present invention, which comprises the impression forming mechanism according to the first, second, or third aspect of the present invention.

According to the hardness testing apparatus of the fourth aspect of the present invention, since the impression forming mechanism of the first, second, or third aspect of the present invention is provided, the sample and the indentor can be contacted mutually such that the force does not easily exceed the preliminary test force at an instant when the sample comes into contact with the indentor, and therefore the working efficiency can be improved. Also, since the force never exceeds the preliminary test force at an instant of contact, the reliability of the result about the hardness testing apparatus can be improved.

In order to accomplish the second object above, the following means are adopted. According to a fifth aspect of the present invention, there is provided a hardness testing apparatus comprising:

a sample table for mounting a sample thereon;

an electromagnetic brake for controlling an elevating operation of the sample table; and a current supplying unit for supplying a current to the electromagnetic brake and inverting a direction of the current supplied to the electromagnetic brake at a predetermined timing.

According to the hardness testing apparatus of fifth aspect of the present invention, since the direction of the current that flows through the electromagnetic brake is inverted at a predetermined timing by the current supplying unit, a magnetic force having the opposite direction is supplied to the sample table, which is magnetized by the drive of the electromagnetic brake, to demagnetize the magnetization of the sample table. Therefore, the sample that is easily attracted by the magnet such as the thin sample, or the like is prevented from being pasted onto the sample table, and the replace of the sample can be conducted effectively.

Here, "immediately after the electromagnetic brake is applied" or "before the sample is exchanged" may be selected as the "predetermined timing". Also, only in the test in which the problem is caused if the sample is magnetized, the current may be inverted manually, or any timing may be given manually.

In the hardness testing apparatus of a sixth aspect of the present invention, according to the fifth aspect of the present invention, it is preferable that the current supplying unit supplies a driving current to drive the electromagnetic brake and then supplies a current, which has an opposite direction to the driving current, in a shorter time than the driving current.

According to the hardness testing apparatus of the sixth aspect of the present invention, after the driving current for driving the electromagnetic brake is supplied by the current supplying unit, the current having the direction opposite to the driving current is supplied in a period that is shorter than that of the driving current. Therefore, the magnetization of the sample table in the opposite direction by supplying the current in the same current supply time as that of the driving current or in the longer time than that of the driving current can be prevented. Thus, the sample table that is magnetized by the drive of the electromagnetic brake can be demagnetized, the sample that is easily attracted by the magnet such as the thin sample, or the like is hard to be pasted onto the sample table, the exchange of the sample can be conducted effectively. Further, the test of the sample, in which the problem is caused if such sample is magnetized can be accomplished.

Here, like the above current supplying unit, the current, the current supply time of which is shorter than the preceding current and which has the direction opposite to that of the preceding current, may be supplied plural times. If doing this, the magnetic force of the sample table can be demagnetized gradually and also the larger demagnetization effect can be achieved.

In the hardness testing apparatus of a seventh aspect of the present invention, according to the sixth aspect of the present invention, it is preferable that the current supplying unit supplies the driving current to the electromagnetic brake in an opposite direction of the prior driving current, which was supplied to the electromagnetic brake, every time when the electromagnetic brake is driven.

According to the hardness testing apparatus of the seventh aspect of the present invention, the current is supplied by the current supplying unit while inverting the direction of the current, which is supplied to the electromagnetic brake, every time when the electromagnetic brake is driven. Therefore, since the currents in the positive and negative directions can be supplied uniformly to the electromagnetic brake, the magnetization of the sample table by the electromagnetic brake is never deviated in one direction, and the demagnetization effect can be obtained much more. The exchange of the sample that is easily attracted by the magnet becomes easy at the time of replace. Further, the test of the sample, in which the problem is caused if such sample is magnetized, can be accomplished.

In order to accomplish the second object above, there is provided a harness testing apparatus comprising:

a sample table for mounting a sample thereon;

an electromagnetic brake for controlling an elevating operation of the sample table; and a high-frequency voltage applying unit for applying a high-frequency voltage to the electromagnetic brake in order to demagnetize the sample table that is magnetized by the electromagnetic brake.

According to the hardness testing apparatus of the eighth aspect of the present invention, there is provided the high-frequency voltage applying unit for applying the high-frequency voltage to the electromagnetic brake to demagnetize the sample table that is magnetized by the drive of the electromagnetic brake. Therefore, the magnetic force of the sample table can be eliminated by the AC demagnetization, the exchange of the sample that is easily attracted by the magnet becomes easy at the time of replace. Thus, not only the test can be conducted effectively but also the test of the sample, in which the problem is caused if such sample is magnetized, can be accomplished.

BRIEF DESCRIPTION OF THE DRAWINGS

FIG. 8 is a side sectional view showing a pertinent configuration of a hardness testing apparatus according to a second embodiment of the present invention;

DETAILED DESCRIPTION OF THE INVENTION

Embodiments of an impression forming mechanism and an impression forming method, and a hardness testing apparatus and a hardness testing method according to the present invention will be explained in detail with reference to the drawings hereinafter.

Figure 1:
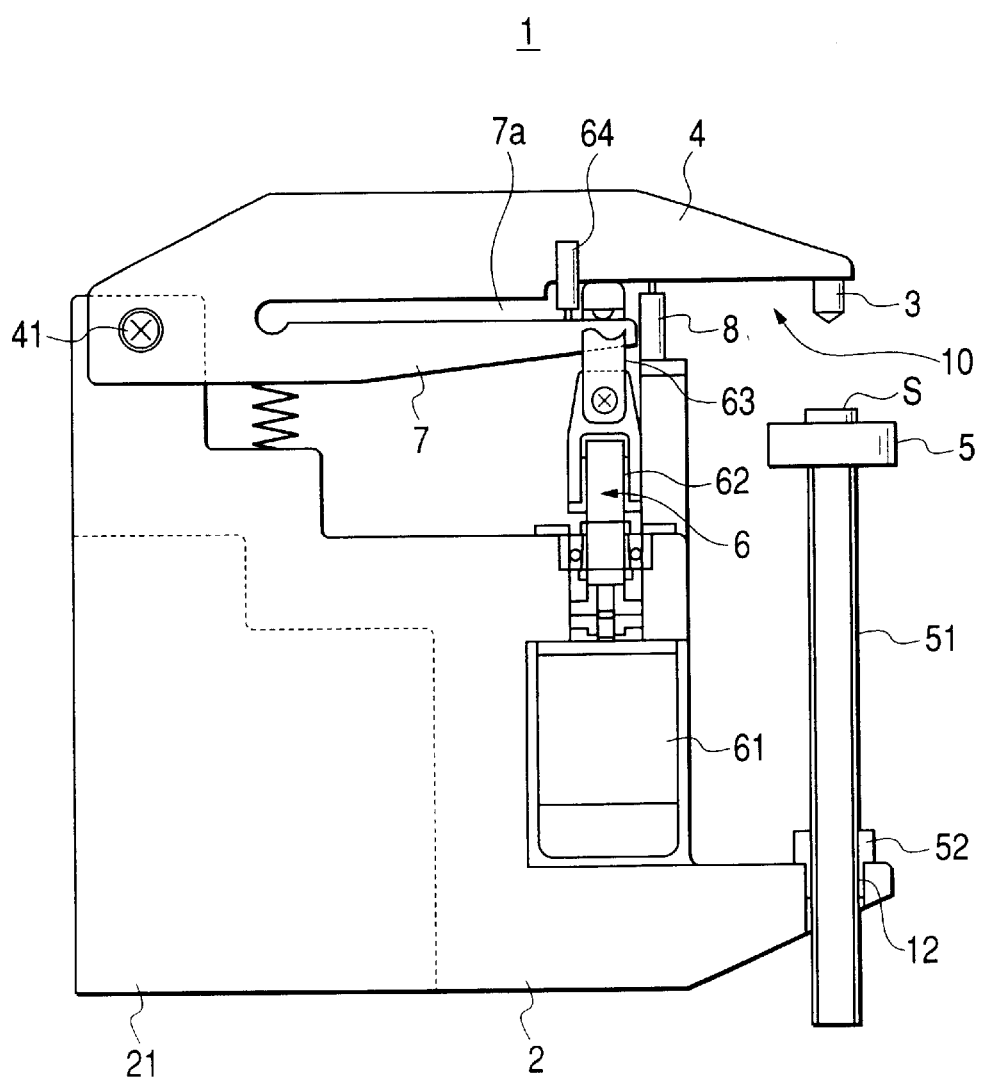
FIG. 1 is a side sectional view showing a pertinent configuration of a hardness testing apparatus according to a first embodiment of the present invention.
Figure 2:
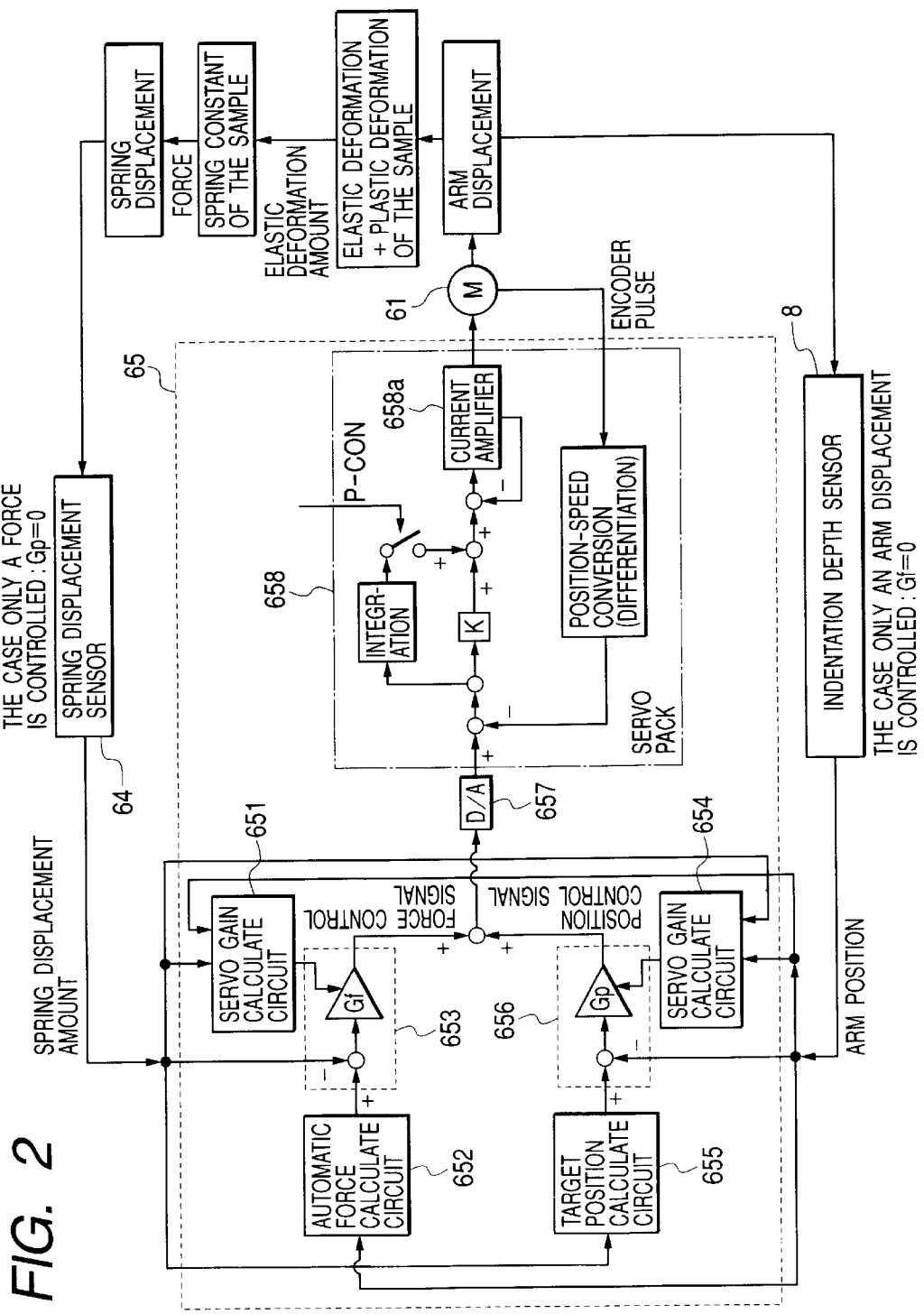
FIG. 2 is a block diagram showing a pertinent configuration of a loading arm operation controlling unit according to the first embodiment of the present invention.
Figure 3:
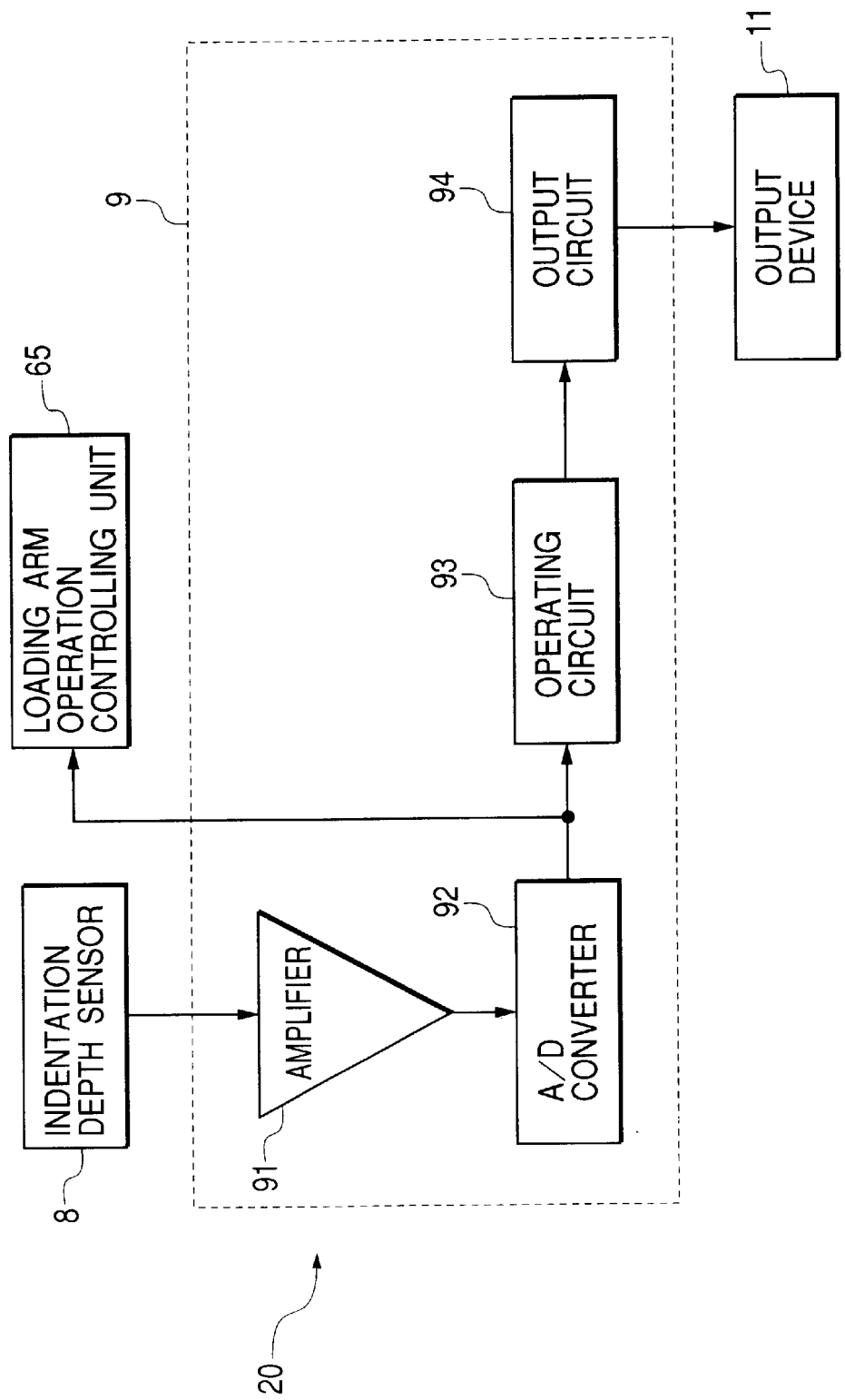
FIG. 3 is a block diagram showing a pertinent configuration of a hardness calculating mechanism part according to the first embodiment of the present invention.

FIG. 1 is a side sectional view showing a pertinent configuration of a hardness testing apparatus according to a first embodiment of the present invention. FIG. 2 is a block diagram showing a pertinent configuration of a loading arm operation controlling unit according to the first embodiment of the present invention. FIG. 3 is a block diagram showing a pertinent configuration of a hardness calculating mechanism part according to the first embodiment of the present invention.

As shown in FIG. 1, a hardness testing apparatus 1 comprises an impression forming mechanism portion 10 comprising a testing apparatus body 2, a loading arm 4, a sample table 5, a loading arm operating part 6, a plate spring 7 or the like. Further, the hardness testing apparatus 1 comprises a hardness calculating mechanism part 20 comprising an indentation depth sensor 8, a hardness calculating unit 9 or the like, as shown in FIG. 3. The loading arm 4 is supported by the testing apparatus body 2 so as to be movable rotationally and has an indentor 3 attached to a free end thereof. The sample table 5 is provided to the testing apparatus body 2 below the indentor 3 and mounts a sample S thereon. The loading arm operating part 6 is provided below the loading arm 4 and moves the free end side of the loading arm 4 rotationally to apply a force (or load) for pressing a surface of the sample S in order to form an impression on the surface of the sample S. The plate spring 7 transmits a force generated by operating the loading arm operating part 6 to the loading arm 4. The indentation depth sensor 8 measures a displacement of the loading arm 4 corresponding to a depth of an impression formed by the indentor 3, on the basis of an opening amount between the testing apparatus body 2 and the loading arm 4. The hardness calculating unit 9 calculates a hardness of the sample S on the basis of the depth of the impression measured by the indentation depth sensor 8. The hardness testing apparatus 1 comprises a force inputting part for inputting a set force which is not shown in the drawings.

The testing apparatus body 2 contains the loading arm operating part 6, a control unit 21 serving as a driving unit for the loading arm operating part 6, etc. in the inside.

The loading arm 4 is supported by the testing apparatus body 2 so as to be movable rotationally by using a crossed spring 41, a rolling bearing or the like. The indentor 3 is attached to the free end of the loading arm 4 so as to be removal therefrom. The loading arm 4 is formed integrally with the plate spring 7. In an initial state, the loading arm 4 is held by a servo motor 61 at a position which is moved downward by a predetermined amount from a horizontal position (or neutral position), (hereinafter the position is referred as a reference position).

A notch 7a is provided between the plate spring 7 and the loading arm 4 along a longitudinal direction thereof. An end of the notch 7a on the indentor 3 side is opened.

A screwed shaft 51 is provided to a bottom surface of the sample table 5. The sample table 5 is attached to the testing apparatus body 2 to move up and down with respect to the testing apparatus body 2 via the screwed shaft 51. The sample table 5 is installed by inserting the screwed shaft 51 into a guide cylinder 12 that is provided to a bottom portion of the testing apparatus body 2. An auto-brake mechanism 52 is provided to an upper portion of the guide cylinder 12. The auto-brake mechanism 52 stops the sample table 5 automatically when the indentor 3 comes into contact with the sample S.

The loading arm operating part 6 includes the servo motor 61 serving as a moving unit, a ball screw 62, and a fixture 63 attached to an end portion of the ball screw 62 and also secured to the plate spring 7. The loading arm operation part 6 is disposed below the loading arm 4. When the bail screw 62 moves up and down by driving the servo motor 61, the loading arm 4 that is formed integrally with the plate spring 7 is moved rotationally.

The fixture 63 connects the loading arm 4 and the loading arm operating part 6. The fixture 63 also has a function of correcting misalignment between an axis of the plate spring 7 and an axis of the loading arm operating part 6, which is caused by the rotational movement of the loading arm 4 and a deformation of the plate spring 7. For example, the fixture 63 has a structure in which a thin plate, a wire, such as a piano wire, or a knife edge is combined with a crossed spring, or in which only a universal joint or the like is used or a universal joint is used in combination with other members.

An operation control of the loading arm 4 is executed by a spring displacement sensor 64 and a loading arm operation controlling unit 65, as shown in FIG. 2. The spring displacement sensor 64 is attached to the loading arm 4 and to the plate spring 7. The spring displacement sensor 64 measures a displacement (or deformation) of the plate spring 7 corresponding to the force applied to the sample S on the basis of an amount of an opening of the notch 7a between the plate spring 7 and the loading arm 4. The loading arm operation controlling unit 65 serving as a force controlling unit receives the spring displacement measured by the spring displacement sensor 64 and controls the operation of the ball screw 62 based on the spring displacement.

The spring displacement sensor 64 comprises a displacement sensor unit (linear scale) that reads optically a glass scale, for example. The spring displacement sensor 64 measures the displacement of the plate spring 7 generated by moving down the ball screw 62 on the basis of an amount of an opening of the notch 7a between the plate spring 7 and the loading arm 4. The spring displacement sensor 64 converts a signal of the spring displacement from analog into digital, and then outputs the digitized spring displacement signal to the loading arm operation controlling unit 65.

As shown in FIG. 2, the loading arm operation controlling unit 65 comprises a servo gain calculate circuit 651, an automatic force calculate circuit 652, a force control circuit 653, a servo gain calculate circuit 654, a target position calculate circuit 655, a loading arm position control circuit 656, a D/A converter 657, a servo motor driving circuit 658, etc.

When the operator brings the sample S into contact with the indentor 3 manually in order to apply the preliminary test force to the sample S, the servo gain calculate circuit 651 receives the digitized spring displacement signal and the arm position signal respectively from the spring displacement sensor 64 and the indentation depth sensor 8. The servo gain calculate circuit 651 calculates values to simulate a condition that the force is applied gradually based on the displacement of the plate spring 7 from an instant when the indentor 3 comes into contact with the sample S, i.e., to control the rotational movement of the loading arm 4 such that after the sample S is brought into contact with the indentor 3, the force is applied gradually to the sample S from the indentor 3 in response to the displacement from the reference position of the loading arm 4 (referred to as "spring control" hereinafter).

The servo gain calculate circuit 651 also receives the digitized spring displacement signal and the arm position signal from the spring displacement sensor 64 and the indentation depth sensor 8 when a test force is applied to the sample S. The servo gain calculate circuit 651 calculates a spring constant of the sample S based on changes in an amount of the force applied to the sample S and an amount of deformation of the sample S in order to decide an initial servo gain. (Gain).

In addition, the servo gain calculate circuit 651 controls the servo gain in such a manner that the serve gain is increased if there is an error (Err) (which is a difference between an actual test force and a target test force, calculated by the following equitation (3)) during a predetermined number of feed-back steps, and the servo gain is decreased to return the initial servo gain if the servo gain exceeds a predetermined value. The calculated servo gain is output to the force control circuit 653.

In this case, a memory (not shown) for storing the calculation results is provided to the servo gain calculate circuit 651.

The automatic force calculate circuit 652 receives the arm position signal from the indentation depth sensor 8, and outputs a target force to be given to the sample in the spring control, or a previously-set target force to the force control circuit 653 as a target force signal.

The force control circuit 653 compares the digitized spring displacement signal corresponding to the force applied to the sample S outputted from the spring displacement sensor 64 with the target force signal (servo motor command data) outputted from the automatic force calculate circuit 652 to form a force control signal that corresponds to a difference between them. Then, the force control circuit 653 adds the servo gain calculated by the servo gain calculate circuit 651 to the force control signal, and outputs a resultant signal to the D/A converter 657. In the drawing, "Gf" is a gain for force control.

The servo gain calculate circuit 654 receives the digitized spring displacement signal and the arm position signal from the spring displacement sensor 64 and the indentation depth sensor 8, and outputs values to execute the spring control, when the operator brings the sample S into contact with the indentor 3 manually in order to apply the preliminary test force to the sample S.

The target position calculate circuit 655 receives the digitized spring displacement signal from the spring displacement sensor 64, and outputs a target position of the loading arm 4 in the spring control, or a previously-set target position to the loading arm position control circuit 656 as a target position signal.

The loading arm position control circuit 656 receives the arm position signal from the indentation depth sensor 8, then compares the arm position signal with the target position signal outputted from the target position calculate circuit 655 to form a position control signal that corresponds to a difference between them. Then, the loading arm position control circuit 656 adds the servo gain calculated by the servo gain calculate circuit 654 to the position control signal, and outputs a resultant signal to the D/A converter 657. In the drawing, "Gp" is a gain for arm position control.

The D/A converter 657 converts the force control signal provided from the force control circuit 653 and the position control signal provided from the loading arm position control circuit 656 from digital into analog, and then outputs them to the servo motor driving circuit 658.

The servo motor driving circuit 658 receives the force control signal and the position control signal which are converted from digital into analog, then amplifies them by a current amplifier 658a with considering adding differential elements and integral elements, and then outputs them to a servo motor 61.

The indentation depth sensor 8, similarly to the spring displacement sensor 64, comprises a displacement sensor unit (linear scale) that reads optically the glass scale, for example, and measures an amount of movement of the loading arm 4 in a vertical direction, which corresponds to the depth of the indentation of the sample S.

The hardness calculating unit 9 comprises an amplifier 91, an A/D converter 92, an operating circuit 93, an output circuit 94, etc, as shown in FIG. 3.

The amplifier 91 amplifies the arm position signal measured by the indentation depth sensor 8 and then the amplified signal to the A/D converter 92. The A/D converter 92 converts the amplified arm position signal from analog into digital and then outputs the digitized arm position signal to the arithmetic circuit 93.

The operating circuit 93 processes the digitized arm position signal according to the operating program stored therein in order to calculate a hardness of the sample S, and then output the hardness data to the output circuit 94. The output circuit 94 converts the calculated hardness data outputted from the operating circuit 93 into the data in a predetermined output format, and then outputs the data to an output device 11 connected to the hardness testing apparatus 1. The output device 11 is, for example, a display device for displaying the hardness data on a screen, a printer device for printing out the hardness data, or the like.

The force control signal or the arm position control signal, that is amplified by the servo motor driving circuit 658, is output to the servo motor 61, and thus the servo motor 61 is driven by the force control signal or the arm position control signal. The ball screw 62 is rotated by driving the servo motor 61 and move upwardly. When the ball screw 62 moves up, the plate spring 7, which is attached to the ball screw 62, and the loading arm 4, which is formed integrally with the plate spring 7 move upwardly in a state that the indentor 3 attached to the free end of the loading arm 4 comes into contact with the sample S being elevated by the operator.

At this time, the spring displacement sensor 64 measures the amount of opening of the notch 7a between the plate spring 7 and the loading arm 4 as the spring displacement signal. Then, the spring displace sensor 64 amplifies the spring displacement signal and outputs the amplified spring displacement signal to the servo gain calculate circuit 651.

Figure 4:
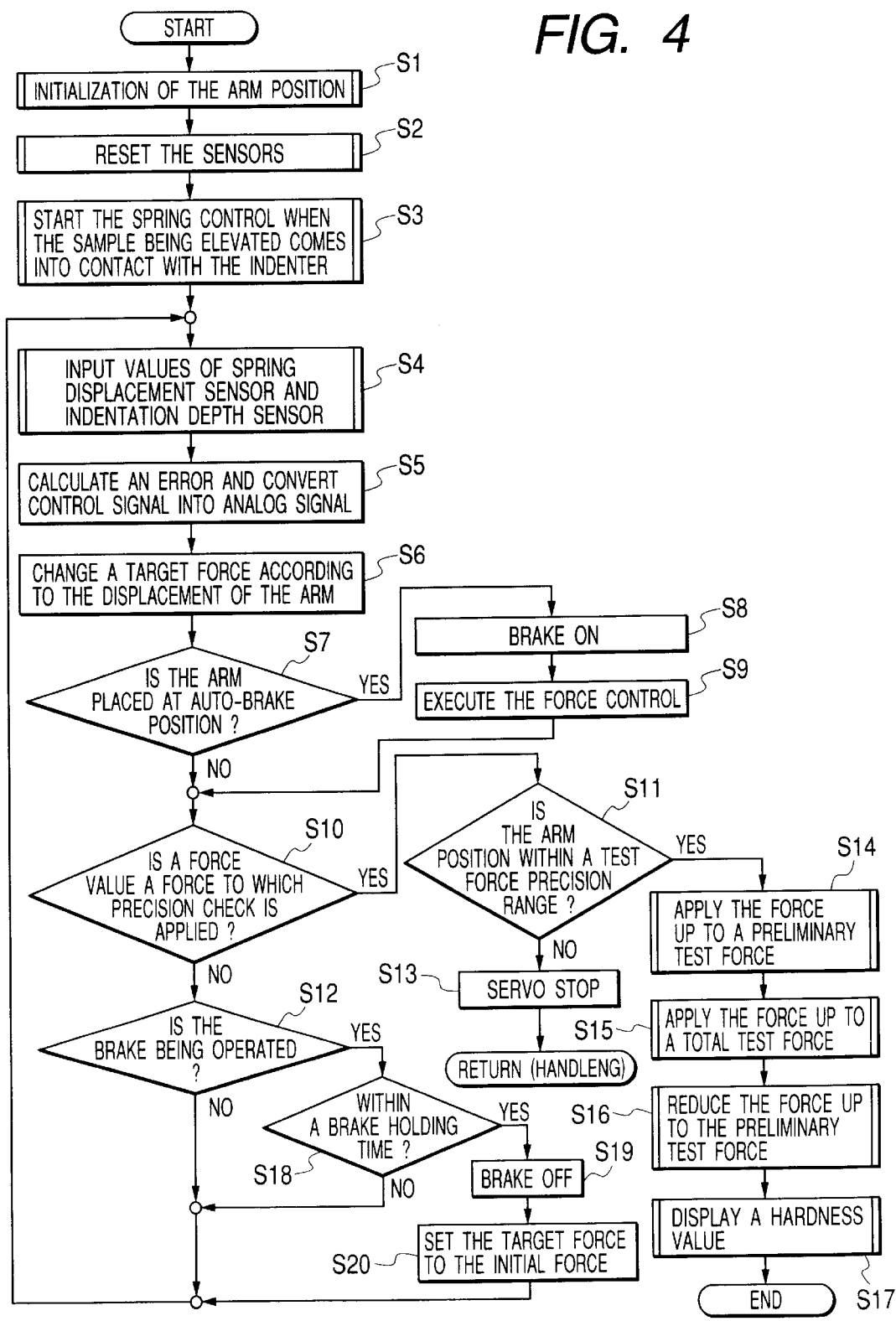
FIG. 4 is a flowchart showing an auto-brake control operation according to the first embodiment of the present invention.

Next, an auto-brake control operation process in the above hardness testing apparatus will be explained by using a flowchart shown in FIG. 4 hereunder.

First, when an auto-braking control process is started, a position of the loading arm 4 is initialized in step S1. That is, a neutral position (or horizontal position) of the loading arm 4 is measured, and then the loading arm 4 is moved downward by a predetermined amount from the neutral position so that the loading arm 4 is set at a reference position.

In step S2, an initialization of a position control of the loading arm 4 is executed. That is, the spring displacement sensor 64 and the indentation depth sensor 8 are reset.

In step S3, when the sample S being elevated by the operator comes into contact with the indentor 3, the spring control is started.

In step S4, read values of the spring displacement sensor 64 and the indentation depth sensor 8 in the present condition are input to the loading arm operation control position 65.

In step S5, an error (Err) which is a difference between an actual arm position and a target arm position is calculated by the loading arm position control portion 656 according to Eq. (1).

$$Err = Gain \times (Arm\ Position) \qquad (1)$$

The D/A converter 657 converts the position control signal based on the error from digital into analog, and then outputs the analog arm position control signal to the servo motor 61 via the servo motor driving circuit 658.

In step S6, a target force is set to a force based on the spring control, according to the displacement of the loading arm 4.

In step S7, it is decided whether or not the arm position measured by the indentation depth sensor 8 is placed at a predetermined position that is lower than the horizontal position by a predetermined amount (referred to as an "auto-brake position" hereinafter). If it is decided that the measured arm position is placed at the auto-brake position, the process goes to step S8 wherein the auto-brake is operated (turned ON) to the sample table 5. The process goes to step S9 where a force control in which the force applied to the sample S at a point of time when the auto-brake is applied is held by controlling the position of the loading arm 4 with respect to the auto-braked sample table 5. Then, the process goes to step S10. In contrast, in step S7, if the arm position measured by the indentation depth sensor 8 is not the auto-brake position, the process goes to step S10. Here, the auto-brake position of the loading arm 4 is such a position that the preliminary test force is fallen within an appropriate precision range when the preliminary test force is applied to the loading arm 4 from the concerned position.

In step S10, it is decided whether or not a value of the force applied to the sample S which is measured by the spring displacement sensor 64 is a value of a force to which a precision check is applied. In other words, it is decided whether or not the force value is larger than a predetermined ratio of the preliminary test force. Then, the process goes to step S11 if it is decided that the force value is larger than the predetermined ratio of the preliminary test force. If it is decided that the force value is smaller than the predetermined ratio of the preliminary test force, the process goes to step S12.

If the process goes to step S11, it is decided here whether or not the position of the loading arm 4 is placed within a range in which a test force precision can be assured. In other words, it is decided whether or not the displacement from the horizontal position of the loading arm 4 is placed within a predetermined test force precision range. Then, if the position of the loading arm 4 is not placed within the predetermined test force precision range, the process goes to step S13 wherein the servo motor 61 is stopped and then process is ended.

On the contrary, if the position of the loading arm 4 is placed within the predetermined test force precision range, in step S14, the auto-brake operated to the sample table 5 is shut off and the force is applied to the sample S up to the preliminary test force by controlling the positions of the loading arm 4 and the sample table 5. Then, the force is applied to the sample S up to a total test force in step S15. After a predetermined time has lapsed, the force applied to the sample S is reduced up to the preliminary test force in step S16. In step S17, a hardness of the sample S is calculated, and a value of the hardness is displayed.

If the process goes to step S12 as the result in step S10, it is decided whether or not the auto-brake is being operated. Then, if it is decided that the auto-brake is not being operated, the process goes to step S4 where the values of the loading arm 4 and the force applied to the sample S, which are changed by elevating the sample table by the operator, are measured by the spring displacement sensor 64 and the indentation depth sensor 8, and inputted to the loading arm operation control position 65 to execute the processes that are subsequent to step S4 once again. In contrast, it is decided that the auto-brake is being operated, the process goes to step S18.

In step S18, it is decided whether or not a period where the auto-brake has been operated is within a brake holding time. If it is decided that the period is not within the brake holding time, the process goes to step S4 and the processes that are subsequent to step S4 are executed once again. While, if it is decided that the period is within the brake holding time, the auto-brake is shut OFF (step S19). Then, the target force is set to the initial force (step S20). Then, the process goes to step S4 and the processes that are subsequent to step S4 are executed once again.

Here, an operation of the loading arm 4 in the spring control will be explained with reference to FIG. 6 hereunder.

Figure 6:
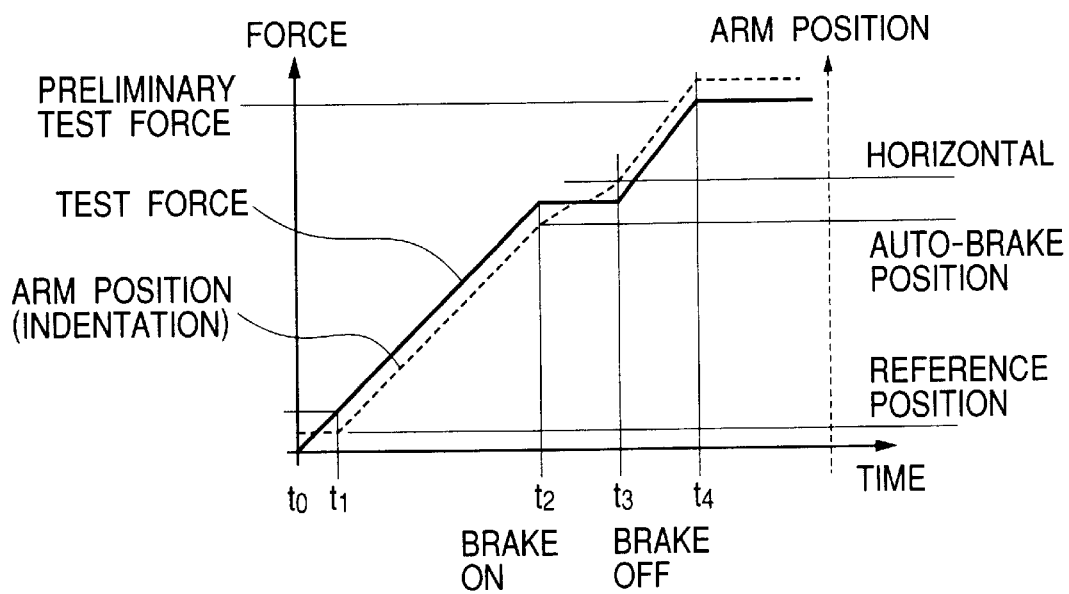
FIG. 6 is a view showing a relationship between an arm position of a loading arm and a force applied to the sample in a spring control.

FIG. 6 is a view showing a relationship between the position of the loading arm 4 and the force applied to the sample S in the spring control. In this FIG. 6, a solid line denotes the force applied to the sample S, and a dotted line denotes the position of the loading arm 4.

In FIG. 6, first, the loading arm 4 is held at the reference position (which is a position that is lower than the horizontal position by a predetermined amount), and the sample S does not contact to the indentor 3 (time t0). Then, when the sample S mounted on the sample table 5 is elevated and brought into contact with the indentor 3 (time t1), the loading arm 4 is moved upwardly in the state that the sample S is brought into contact with the indentor 3. At this time, the force applied to the sample S from the indentor 3 is increased (time t1→time t2) while the position of the loading arm 4 is changed from the reference position. Then, in step S7, if it is decided that the position of the loading arm 4 comes up to the auto-brake position, the auto-brake is operated (time t2) to the sample table 5 and the loading arm 4 is controlled to hold the force applied to the sample S at this time in accordance with the position of the auto-braked sample table 5. Then, the loading arm 4 is moved upwardly once again (time t3) via step S9, step S11, and step S14, and the preliminary test force is applied to the sample S at a predetermined position from the horizontal position (time t4).

Figure 7A:
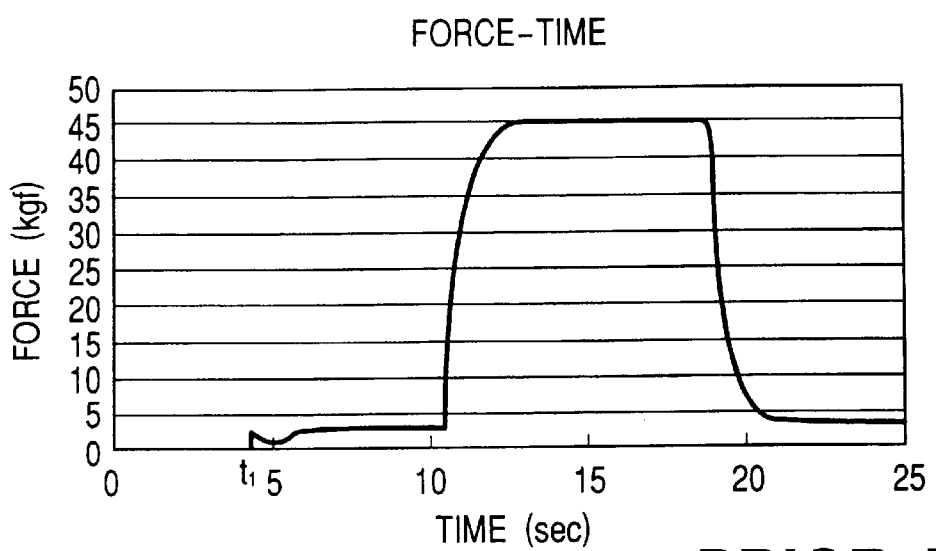
FIG. 7A is a view showing a force applied to a sample when an indentor comes into contact with the sample, in the case of the hardness testing apparatus in the related art.
Figure 7B:
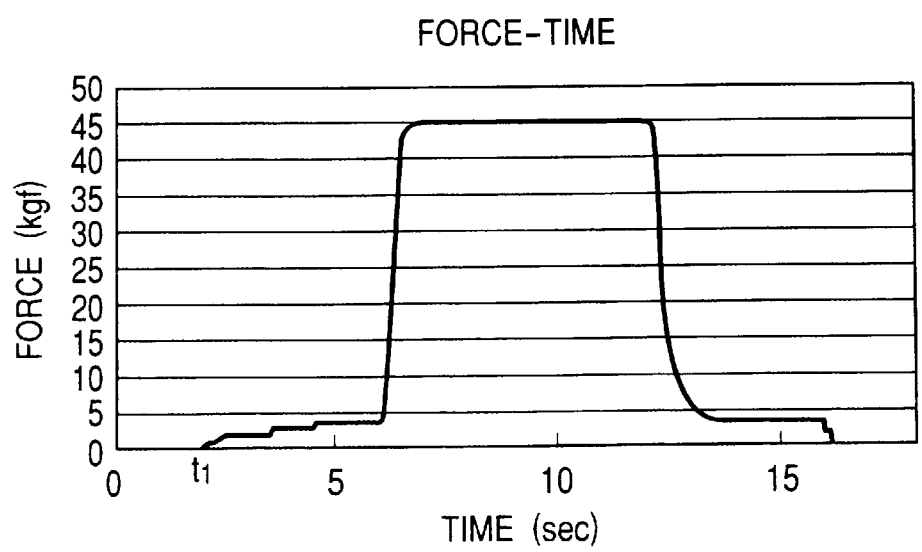
FIG. 7B is a view showing a force applied to a sample when an indentor comes into contact with the sample, in the case of the hardness testing apparatus according to the first embodiment of the present invention.

If the above spring control is carried out, the impact of the indentor 3 to the sample S can be reduced rather than the related-art method that the indentor 3 is brought into contact with the sample S in the state that the loading arm 4 is fixed. Thus, such a problem can be overcome that the force applied to the sample S exceeds the preliminary test force. For example, in the case of the hardness testing apparatus in which a small test force is applied to the sample, like the superficial hardness testing apparatus, the above spring control is particularly effective. FIG. 7A is a view showing the force applied to the sample when the indentor comes into contact with the sample, in the case of the hardness testing apparatus in the related art. FIG. 7B is a view showing the force applied to the sample when the indentor comes into contact with the sample, in the case of the hardness testing apparatus 1 of the present invention. In FIG. 7A, the impact where the force comes up to around the preliminary test force is applied to the sample S at an instant when the indentor 3 comes into contact with the sample S (time t1). In contrast, in FIG. 7B, the impact is not applied to the sample S at an instant when the indentor 3 comes into contact with the sample S (time t1), and the force is gradually applied to the sample S.

Figure 5:
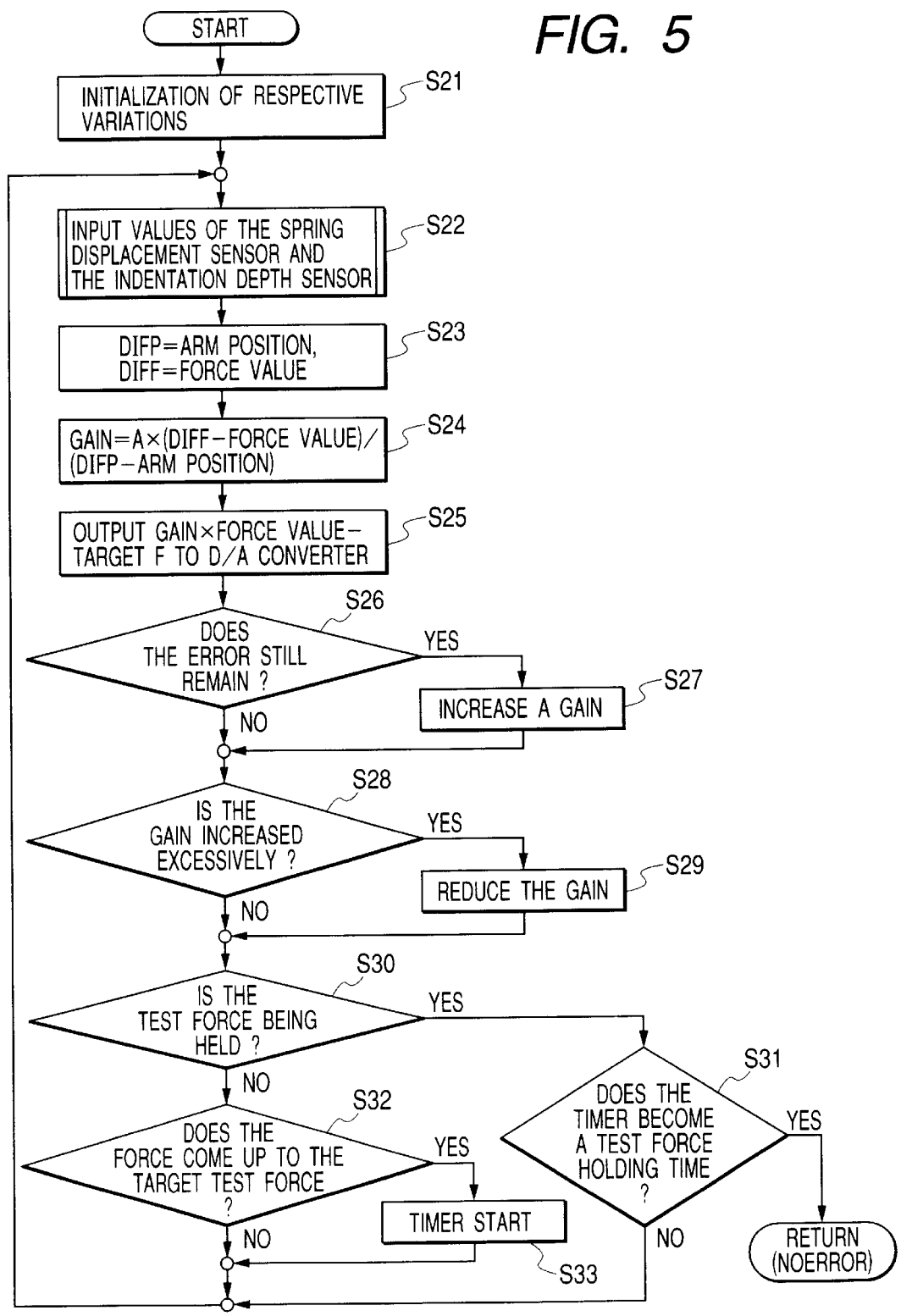
FIG. 5 is a flowchart showing a test force control operation according to the first embodiment of the present invention.

Next, a test force control operation by the above hardness testing apparatus will be explained with reference to a flowchart shown in FIG. 5.

First, the power supply is turned ON, the initialization of respective variations is executed in step S21. More particularly, values of respective variations of servo-gain (Gain), error (Err), arm position (DIFP), force value (DIFF), etc. are initialized. Then, a value of a target force (Target F) is input into a force inputting part (not shown).

In step S22, values of the spring displacement sensor 64 and the indentation depth sensor 8 in the present condition are input into the servo gain calculate circuit 651. Then, these values are stored in a memory (not shown) that is built in the servo gain calculate circuit 651 (step S23). This is because these values are to be used for the force control in the next routine.

In step S24, a predetermined test force is applied to the sample S to decide an initial servo gain. Then, when the arm position at this time is input into the servo gain calculate circuit 651, the initial servo gain is decided by Eq.(2).

$$Gain = A \times (DIFF\text{-}force\ value)/(DIFF\text{-}arm\ position) \qquad (2)$$

Where A: any constant.

In step S25, the error (Err), i.e., a difference between a value of the actual force value and a value of the target force value is calculated by Eq. (3).

$$Err = Gain \times (force\ value) - Target\ F \qquad (3)$$

In step S26, it is decided whether or not there is still the error. In other words, it is decided whether or not the difference between the error (Err1) measured in the preceding feed-back routine and the error (Err) measured at this time is "0". Then, the process goes to step S27 if such difference is "0" whereas the process goes to step S28 as it is unless such difference is "0".

In case it is decided whether or not there is still the error, it may be decided that there is still the error when the difference between the errors becomes successively "0" in the feed-back routines by a predetermined number of times (e.g., five times).

In step S27, a process of increasing the servo gain by a predetermined value is executed, and then the process goes to step S28. At step 27, the servo gain may be increased stepwise.

In step S28, it is decided whether or not the servo gain exceeds an allowable upper limit value. If the servo gain exceeds the allowable upper limit value, the process goes to step S29 wherein the process of reducing the servo gain by a predetermined value is executed, and then the process goes to step S30. In contrast, if the servo gain does not exceed the allowable upper limit value, the process goes to step S30.

In step S30, it is decided whether or not the test force is being maintained. If it is decided that the test force is being maintained, the process goes to step S31. While, if it is decided that the test force is not being maintained, the process goes to step S32.

If the process goes to step S32, it is decided whether or not the force applied to the sample S come up to a target test force. If the force applied to the sample S does not reach the target test force, the process goes back to step S22 and then the processes are repeated once again. While, if the test force applied to the sample S reaches the target test force, a timer which measures a period where the test force has been applied to the sample S is started in step S33. Then, the process goes back to step S22 and then the processes subsequent to step S22 are continued.

In contrast, if the process goes to step S31 as the result of decision in step S30, it is decided whether or not the timer becomes a test force holding time. If the timer does not become the test force holding time, the process goes back to step S22 and then the process is continued. While, if the timer becomes the test force holding time, the test force application and hold operations are ended.

Then, after the test force control operation is ended, a depth of the impression is measured by the indentation depth sensor 8 as the arm position signal. This arm position signal is amplified by the amplifier 91, then converted from analog into digital by the A/D converter 92, and then output to the operating circuit 93.

Then, the operating circuit 93 processes the digitized arm position signal according to the operating program stored therein in order to calculate a hardness of the sample S. The calculated hardness data is outputted from the predetermined output device 11 via the output circuit 94.

According to the impression forming mechanism 10 and the hardness testing apparatus 1 of the present invention, which are explained as above, the spring control of the loading arm 4 is started from an instant when the sample S is brought into contact with the indentor 3. In other words, after the sample S is brought into contact with the indentor 3, the rotational movement of the loading arm 4 is controlled such that the force is applied gradually from the indentor 3 to the sample S in response to the displacement of the loading arm 4 from the reference position.

As a result, when the sample S is brought into contact with the indentor 3, the force can be applied gradually not to apply the impact to the sample S. Thus, there can be overcome the problem such that the force that excesses the preliminary test force is generated at an instant when the sample S is brought into contact with the indentor 3.

Further, since the operation of the spring control of the loading arm 4 is controlled by the servo motor 61, etc., the operations for various spring constants of the sample S can be simulated. Thus, an appropriate spring constant can be easily accomplished according to various conditions such as the hardness of the sample S, etc. in contrast to the case the elastic substance such as the spring, or the like is employed actually.

In addition, if the operator executes only the operations of the handle, etc. in the same manner as the related art when such operator elevates the sample table 5 to bring the sample S into contact with the indentor 3, the more appropriate working result can be implemented. Therefore, the substantial improvement of the operability can be achieved.

In this case, in the above embodiment, the timing to start the spring control is set to an instant when the sample S is brought into contact with the indentor 3. However, if a distance sensing unit (distance sensor, or the like) for sensing a distance between the indentor 3 and the sample S is provided, the loading arm 4 may be moved at an appropriate speed at a point of time when the sample S comes close to the indentor 3 within a predetermined distance. In this case, the impact generated at an instant when the sample S comes into contact with the indentor 3 can be reduced further more.

Figure 9:
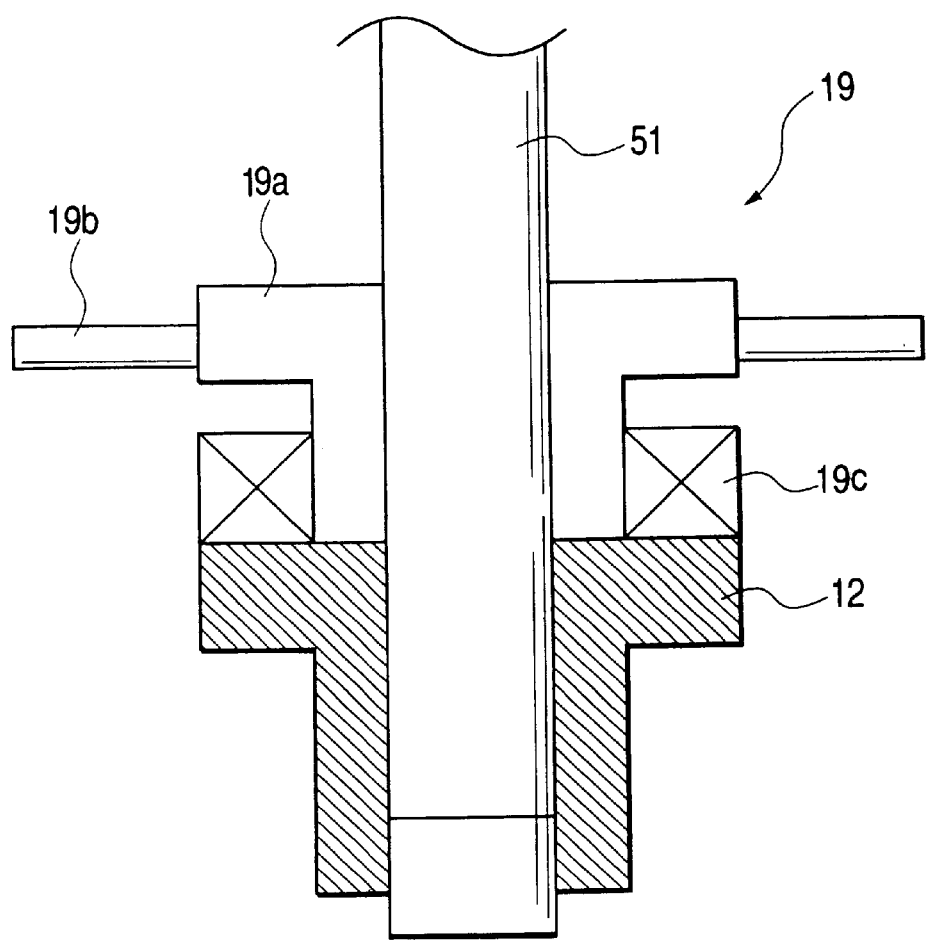
FIG. 9 is a side sectional view showing a configuration of an electromagnetic brake employed in the hardness testing apparatus of FIG. 8.

A second embodiment of the present invention will be explained with reference to the drawings hereinafter. In the second embodiment of the present invention, members and portions similar to the first embodiment are designated by the same reference numbers in FIGS. 1–3, and descriptions thereon are omitted. As shown in FIG. 8 and FIG. 9, for example, a hardness testing apparatus 1 according to the second embodiment of the present invention, comprises an impression forming mechanism portion 10 comprising a testing apparatus body 2, a loading arm 4, a sample table 5, a loading arm operating part 6, a plate spring 7 or the like. The loading arm 4 is supported by the testing apparatus body 2 so as to be movable rotationally, and has an indentor 3 attached to a free end thereof. The sample table 5 is provided to the testing apparatus body 2 below the indentor 3 and mounts a sample S thereon to elevate. The loading arm operating part 6 is provided below the loading arm 4 and moves the free end side of the loading arm 4 rotationally to apply a force (or load) for pressing a surface of the sample S in order to form an impression onto the surface of the sample S. The plate spring 7 transmits a force generated by operating the loading arm operating part 6 to the loading arm 4. The hardness testing apparatus 1 also comprises an electromagnetic brake 19 for stopping the elevating operation of the sample table 5, and a control portion 22 for controlling an operation of the electromagnetic brake 19.

The testing apparatus body 2 contains the loading arm operating part 6, a control unit 21 serving as a driving unit for the electromagnetic brake 9, etc. in the inside. The control unit 21 serves as a power supply source, and builds a power converting device 21a, such as the cycloconverter, the inverter, or the like therein to execute a conversion and a control of the power that is supplied in response to a control signal transmitted from the control portion 22.

The loading arm 4 is supported by the testing apparatus body 2 so as to be movable rotationally by using a crossed spring 41, a rolling bearing, or the like. The indentor 3 is attached to the free end of the loading arm 4 so as to removable therefrom. The loading arm 4 is formed integrally with the plate spring 7.

A notch 7a is provided between the plate spring 7 and the loading arm 4 along a longitudinal direction. An end of the notch 7a on the indentor 3 side is opened.

The loading arm 4 comprises a spring displacement sensor 64, and an indentation depth sensor 8. The spring displacement sensor 64 measures a displacement (or deformation) of the plate spring 7 corresponding the force applied to the sample S on the basis of an mount of an opening the notch 7a between the loading arm 4 and the plate spring 7. The indentation depth sensor 8 measures a displacement of the loading arm 4 corresponding to a depth of an impression formed by the indentor 3, on the basis of an opening amount between the testing apparatus body 2 and the loading arm 4.

The sample table 5 is formed of a circular plate, for example, and a screwed shaft 51 for supporting the sample table 5 is provided to a bottom surface of the sample table 5.

The sample table 5 is installed by inserting the screwed shaft 51 into a guide cylinder 12 that is provided to a bottom portion of the testing apparatus body 2.

The electromagnetic brake 19 is provided to an upper portion of the guide cylinder 12. The electromagnetic brake 19 comprises a nut 19a into which the screwed shaft 51 is inserted, a handle 19b provided to project horizontally from an upper portion of the nut 19a, an electromagnet 19c provided between the nut 19a and the guide cylinder 12, etc.

A screwed hole that is engaged with a screw portion of the screwed shaft 51 is formed in the inside of the nut 19a. Thus, the sample table 5 can be elevated toward the indentor 3 by rotating the handle 19b in one direction, and the sample table 5 can be pulled down by rotating the handle 19b in the other direction.

The electromagnet 19c provided below the nut 19a is connected to the control unit 21, and the current supplied to the electromagnet 19c is controlled by the control portion 22. When a predetermine force is applied to the sample S, a current is supplied to the electromagnet 19c to stop the rotational motion of the nut 19a.

Both the current in the positive direction and the current in the opposite direction can be supplied to the electromagnet 19c from the control portion 22 such that the electromagnet 19c can be magnetized and demagnetized.

The loading arm operating part 6 comprises of a servo motor 61, a ball screw 62, and a fixture 63 fitted to an end portion of the ball screw 62 and also secured to the plate spring 7. When the ball screw 62 moves up and down by driving the servo motor 61, the loading arm 4 that is formed integrally with the plate spring 7 is moves rotationally.

The control portion 22 executes a control of a voltage and a current supplied to the electromagnetic brake 19, which are provided to the lower portion of the sample table 5, in response to the present force value that is transmitted from the spring displacement sensor 64.

More particularly, the control portion 22 compares a predetermined operating force value of the electromagnetic brake 19 with the force value that is transmitted from the spring displacement sensor 64. Then, when the force value transmitted from the spring displacement sensor 64 comes up to the predetermined force value, the control portion 22 turns ON a switch of the electromagnetic brake 19 to supply the current to the electromagnet 19c, and thus the nut 19a that is provided to the upper portion of the electromagnet 19c is caused to stop its rotational motion.

In order to prevent the magnetization of the sample table 5 by employing the electromagnetic brake 19, the control portion 22 executes the demagnetization of the sample table 5 by using two methods described in the following.

The first method is such a method that the direction of the current flowing through the electromagnet 19c is inverted.

More particularly, after the electromagnetic brake 19 is driven, the demagnetization of the sample table 5 that is magnetized by the electromagnet 19c can be executed by supplying the current, the direction of which is opposite to the current used to drive the electromagnetic brake 19, to the electromagnet 19c in a time that is shorter than an electromagnetic brake driving time, and then supplying repeatedly the current in the direction, which is opposite to that of the preceding current, in a short time at plural times (this current being applied at plural times is called a demagnetization current).

In addition, the direction of the driving current for driving the electromagnetic brake 19 is inverted every brake operation such that positive and negative currents are applied to the electromagnetic brake 19 at the same rate in order not to magnetize the electromagnet 19c in one direction.

Figure 10:
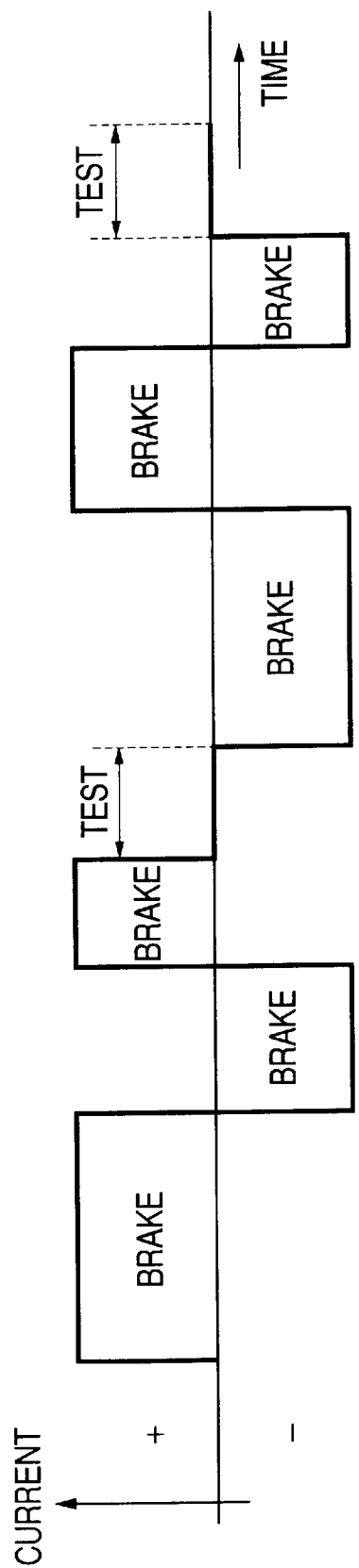
FIG. 10 is a view showing a change of a current applied to the electromagnetic brake when the electromagnetic brake is driven.

For example, as shown in FIG. 10, the control portion 22 inverts sequentially the directions of the driving current of the electromagnetic brake 19, and a demagnetization current of the sample table 5. Then, the sample table 5 that is magnetized by the driving current of the electromagnetic brake 19 is demagnetized by supplying the demagnetization current. Also, the driving current of the electromagnetic brake 19 is inverted such that the positive and negative currents can be applied to the electromagnetic brake 19 at the same rate, so that the demagnetization effect of the sample table 5 can be enhanced.

Figure 11A:
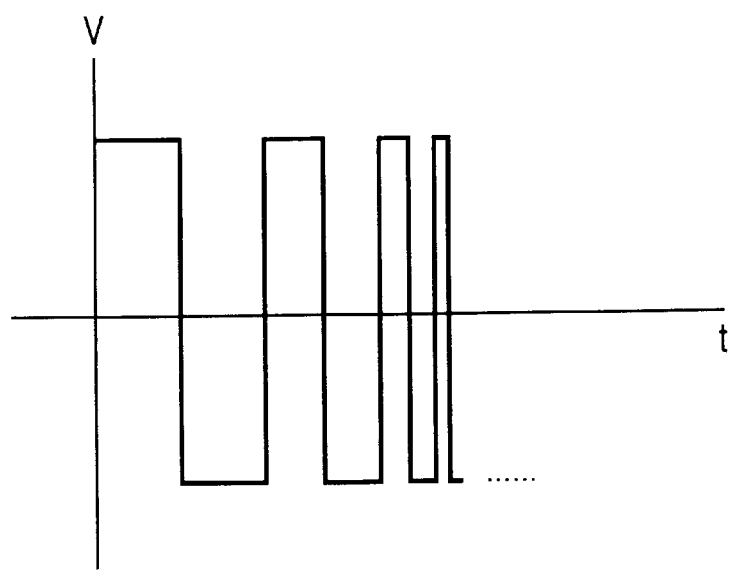
FIG. 11A is a view showing transitions of a voltage supplied to the electromagnetic brake when a test is ended.
Figure 11B:
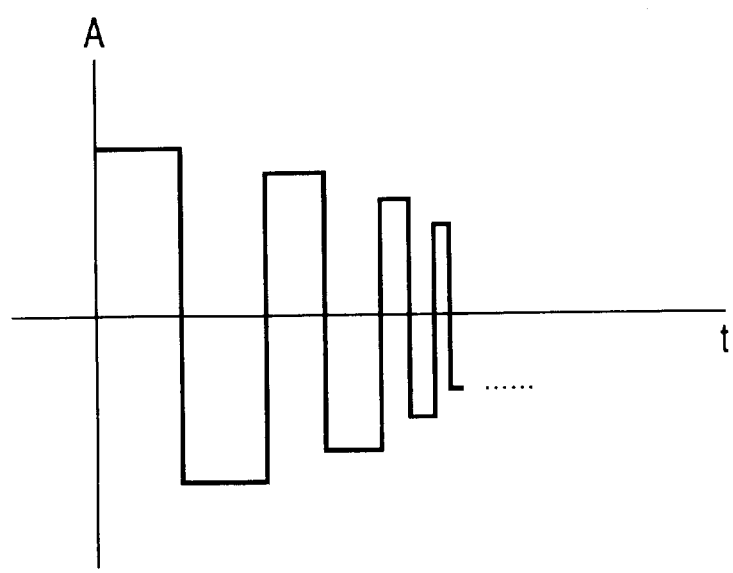
FIG. 11B is a view showing transitions of a current supplied to the electromagnetic brake when a test is ended.

The second method is such a method that the sample table 5 is demagnetized completely by applying a voltage of a high frequency to the electromagnet 19c immediately after the electromagnetic brake 19 is operated or before the test is ended. The control portion 22 supplies the voltage with a predetermined magnitude, as shown in FIG. 11A, to the electromagnetic brake 19, and then increases a frequency of this voltage gradually, by transmitting a control signal to the power converter device 21a, that is built in the control unit 21. The current, which is supplied to a coil of the electromagnet 19c, is decreased gradually as shown in FIG. 11B, and finally the current that is supplied to the coil of the electromagnet 19c is eliminated, so that the sample table 5 is demagnetized completely.

In addition, in addition to the above control of the electromagnetic brake 19, the control portion 22 executes electrical controls about the operation of the hardness testing apparatus 1 such as setting of the test force control of the loading arm 4, calculation of the test result, etc. in compliance with the program, which is stored in an internal memory device of the control portion 22.

Figure 12:
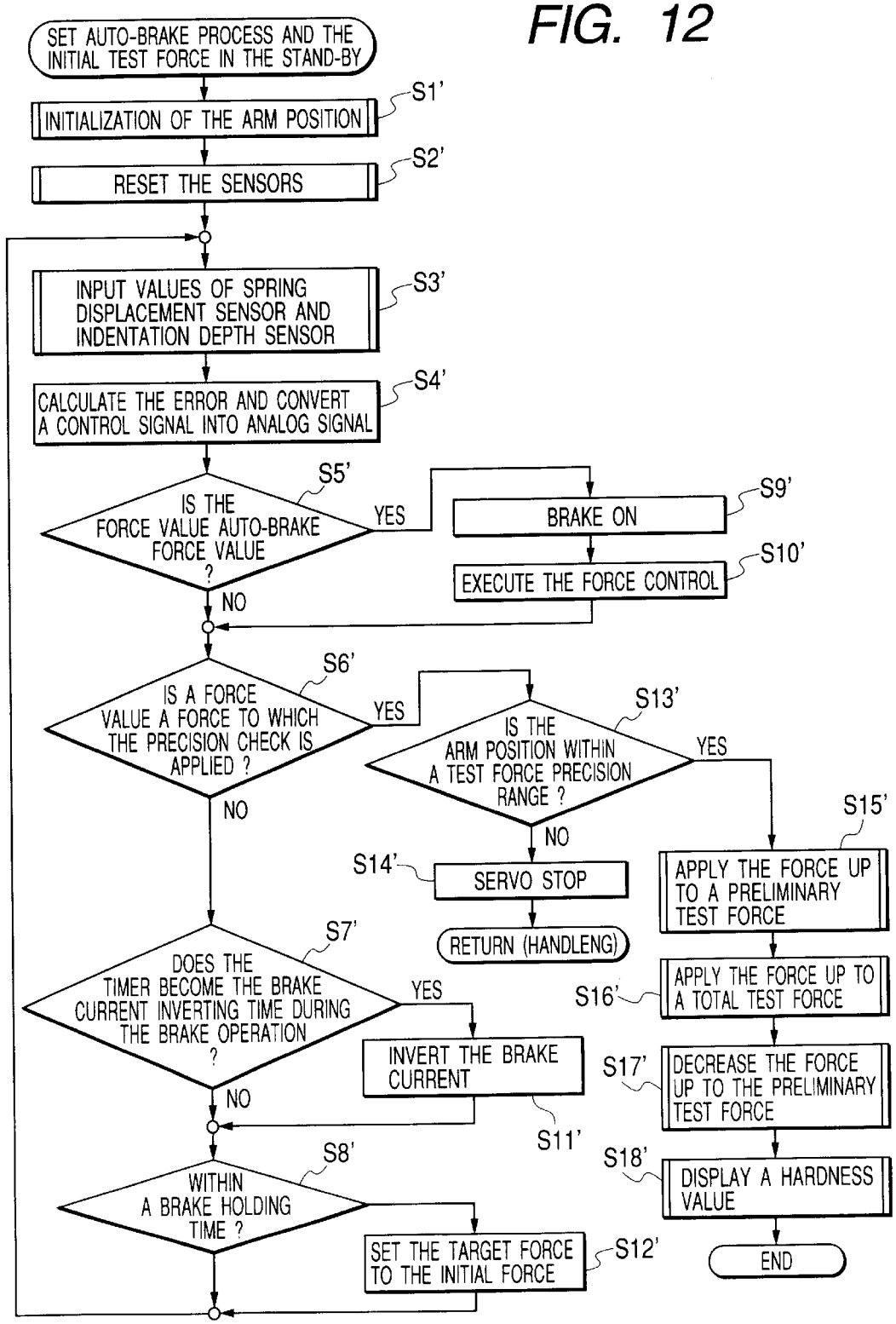
FIG. 12 is a flowchart explaining an operation of the electromagnetic brake according to a second embodiment of the present invention.
Figure 13:
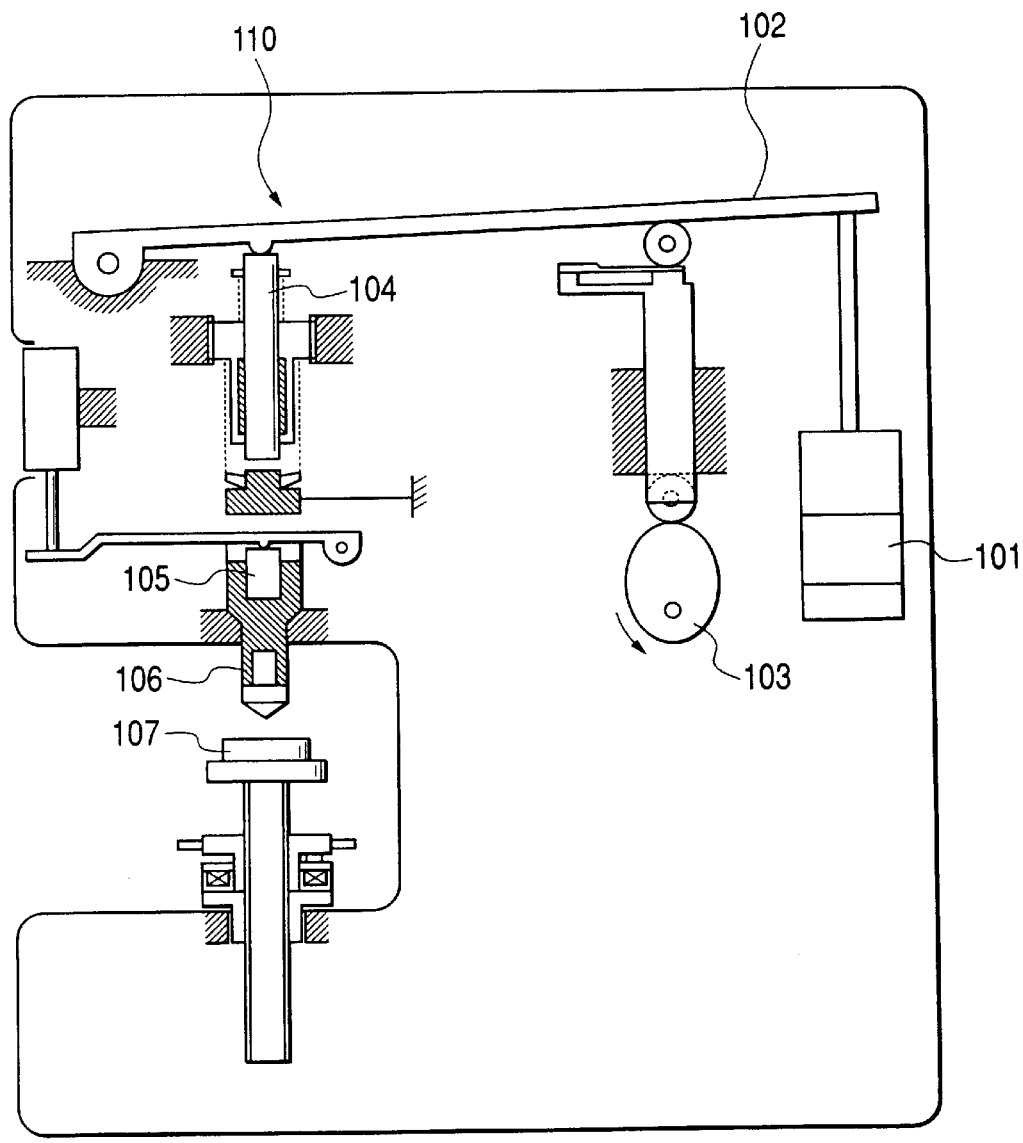
FIG. 13 is a side view showing a pertinent configuration of the hardness testing apparatus in the related art.

Next, a testing operation of the Rockwell type hardness testing machine 1 in the above configuration will be explained in compliance with a flowchart shown in FIG. 12.

First, when a switch of the Rockwell type hardness testing machine 1 is turned ON and a preliminary test force value and a test force value are input from an input portion (not shown), initialization of a position of the loading arm 4 is executed in step S1'. That is, the control portion 22 senses a neutral position of the loading arm 4, supplies a force signal to the servo motor 61 to move the loading arm 4 downwardly from the neutral position by a predetermined amount so as to set the loading arm 4 to a reference position.

In step S2', a value of the spring displacement sensor 64 is reset and a force value for operating the electromagnetic brake 19 (referred to as an "auto-brake load" hereinafter) is set by subtracting a predetermined value from the input preliminary test force value.

As described above, when the position of the loading arm 4 is set and data in the control portion 22 are initialized; the operator elevates the sample table 5 by rotating the nut 19a, which is provided to the lower portion of the sample table 5; by the handle 19b. The control portion 22 goes to the PID control in which a target amount is input as a value of the auto-brake force and a control amount is input as a value of the spring displacement sensor 64, in order to set the sample table 5 to the predetermined position.

In other words, the control portion 22 converts the value of the spring displacement sensor 64 and the value of the indentation depth sensor 8 at this time point into the digital data by the A/D converter (not shown), and then stores the data in the control portion 22 (step S3'). In step S4', the control portion 22 calculates an error based on the value of the spring displacement sensor 64 stored in the control portion 22 and the force value supplied from the servo motor 61 to the plate spring 7. Then, the control portion 22 converts the control signal to be supplied to the servo motor 61 based on the error from digital into analog, then amplifies the resultant signal by the driving circuit (not shown), and then outputs the signal to the servo motor 61.

In step S5', it is decided whether or not the force value measured by the spring displacement sensor 64 is a force value at which the electromagnetic brake 19 is driven (the auto-brake force). If the force value is not the value at which the electromagnetic brake 19 is operated (step S5'; NO), the process goes to the step S6'. In this case, since the switching of the force control in step S10 has not been yet, the precision check of the force value becomes NO (step S6'; NO), and then the process goes to step S7'. Further, since the switch of the electromagnetic brake 19 has not been turned ON yet in step S7' and step S8', the precision check becomes NO and the operation of the control portion goes to step S3' where the values of the loading arm 4 and the force applied to the sample S, which are changed by elevating the sample table by the operator, are measured by the spring displacement sensor 64 and the indentation depth sensor 8 to execute the processes that are subsequent to step S3' once again.

As described above, the sample table 5 is elevated by repeating the loop process from step S3' to step S8' plural times in response to the operator's elevating operation of the sample table. If the auto-brake force is applied between the sample S on the sample table 5 and the indentor 3 (step S5'; YES), the electromagnetic brake 19 is turned ON and also the control portion 22 supplies the current to the electromagnet 19c in the electromagnetic brake 19 to stop the operator's rotating operation of the nut 19a (step S9'). Then, the control portion 22 set a brake holding time and a brake current inverting time in a timer, and switches the control to the force control which the force applied to the sample S at a point of time when the auto-brake is applied is held by controlling the position of the loading arm 4 with respect to the auto-braked sample table 5 (step S10').

Then, if it is decided that the force value does not correspond to the force to which the precision check is applied (step S6'; NO) and the process goes to step S7' during the operation of the electromagnetic brake, it is decided by the control portion 22 whether or not the timer becomes the brake current inverting time during the operation of the brake (step S7'). If it is decided that the timer becomes the brake current inverting time (step S7'; YES), first the control portion supplies the electromagnetic brake driving current to the electromagnet 19c in the electromagnetic brake 19 and then supplies repeatedly the current plural times in a short time in the direction opposite to that of the preceding current (step S11'). Thus, the sample table 5 that is magnetized by the electromagnet 19c can be demagnetized.

In contrast, if it is decided that the brake current inverting time is ended (step S7'; NO), the process goes to step S8 wherein it is decided by the control portion 22 whether or not a period where the auto-brake has been operated is within the brake holding time. Then, if it is decided that the period where the auto-brake has been operated is within the brake holding time (step S8'; YES), the control portion 22 turns OFF the electromagnetic brake 19 and then sets the target force is set to the initial force (step S12'). Thus, the operations subsequent to step S3' are executed repeatedly.

Then, if the process goes to step S6' in this state, the decision in step S6' becomes YES and then the process goes to step S13'.

In step S6', the control portion 22 compares the value measured by the spring displacement sensor 64 with the value set in step S12 to decide whether or not the value measured by the spring displacement sensor 64 is the value within the range in which the precision check is applied. Then, if the value measured by the spring displacement sensor 64 corresponds to the value to which the precision check is applied (step S6'; YES), the control portion 22 receives the displacement of the arm from the indentation depth sensor 8. If the arm position of the loading arm 4 is too high or too low (step S13'; NO), the control portion 22 stops the servo motor 61 (step S14'). Thus, the test is ended.

While, if the position of the loading arm 4 is within the test force precision range (step S13'; YES), the control portion 22 drives the servo motor 61 to move the loading arm to a predetermined position and also applies the preliminary test force to the sample (step S15'), then drives the servo motor 61 to pull down the loading arm 4 and then applies a total test force to the sample S (step S16'), then elevates the loading arm 4 to return the force applied to the sample S to the preliminary test force (step S17'). The control portion 22 then calculates the hardness value based on the displacement of the loading arm 4 and then displays the hardness value on the display portion (not shown) (step S18').

Then, a voltage having a predetermined magnitude is supplied to the electromagnetic brake 19 at the time when the test is ended, and then a frequency of the voltage is increased gradually. Then, the current supplied to the coil of the electromagnet 19c is decreased gradually, and finally the current flowing through the coil of the electromagnet 19c is eliminated perfectly, whereby the sample table 5 may be completely demagnetized.

As described above, in the Rockwell type hardness testing machine 1 in the present embodiment, the demagnetization of the electromagnet 19c in the electromagnetic brake 19 is carried out by supplying repeatedly the current plural times in a short time in the direction opposite to that of the preceding current after the electromagnetic brake 19 is driven. Further, the direction of the driving current is inverted every operation of the electromagnetic brake 19 such that the positive and negative currents can be supplied to the electromagnetic brake 19 at the same rate. Thus, the magnetization of the sample table 5 can be prevented.

Also, in the above Rockwell type hardness testing machine 1, the voltage having the predetermined magnitude is supplied to the electromagnet 19c in the electromagnetic brake 19 when the test is ended, and then the frequency of this voltage is increased gradually not to supply the current to the coil of electromagnet 19c. Thus, the magnetization of the sample table 5 can be prevented.

Accordingly, in the Rockwell type hardness testing machine 1 in the present embodiment, the attraction of the thin sample to the sample table 5 can be prevented by preventing the magnetization of the sample table 5 that is provided to the upper portion of the electromagnet 19c. Therefore, the exchange of the sample can be facilitated and also the test of the sample in which the problem is caused if such sample is magnetized can be attained.

In this case, the present invention is not limited to the above embodiments. The modification, the improvement, etc. within the scope to attain the object of the present invention may be contained in the present invention.

For example, the Rockwell type hardness testing machine is explained in the above embodiments. But there is no necessity that the present invention should be limited to the Rockwell type hardness testing machine. The present invention may be applied to the Brinell type hardness testing machine or the Vickers type hardness testing machine, for example, if such testing apparatus has the mechanism for controlling the vertical movement of the sample table.

Also, it is not always needed that the elevating operation of the sample table should be executed manually. The sample table may be elevated automatically by the motor, or the like.

Also, in the second embodiment, the switch of the electromagnetic brake is turned ON when the predetermined force is applied to the sample on the sample table. But the present invention is not limited to the control by using the force. For instance, the control by using the distance between the indentor and the sample may be executed, and the electromagnetic brake may be applied at a point of time when the sample comes close to the indentor within a predetermined distance. If doing so, the impact generated at an instant when the sample comes into contact with the indentor can be reduced. Therefore, there can be overcome the problem such that the force exceeds the preliminary test force at an instant of contact.

What is claimed is:

1. A hardness testing apparatus comprising:

a sample table for mounting a sample thereon;

an electromagnetic brake for controlling an elevation operation of the sample table; and a current supplying unit for supplying a current to the electromagnetic brake and inverting a direction of the current supplied to the electromagnetic brake at a predetermined timing.

2. The hardness testing apparatus according to claim 1, wherein the current supplying unit supplies a driving current to drive the electromagnetic brake and then supplies a current, which has an opposite direction to the driving current, in a shorter time than the driving current.

3. The hardness testing apparatus according to claim 2, wherein the current supplying unit supplies the driving current to the electromagnetic brake in an opposite direction of the prior driving current, which was supplied to the electromagnetic brake, every time when the electromagnetic brake is driven.

4. The hardness testing apparatus according to claim 1, further comprising:

a high-frequency voltage applying unit for applying a high-frequency voltage to the electromagnetic brake in order to demagnetize the sample table that is magnetized by the electromagnetic brake.

5. The hardness testing apparatus according to claim 4, further comprising:

an impression forming mechanism for forming an impression on a surface of a sample with an indentor, the impression forming mechanism having an impact reducing unit for controlling a movement of one of the sample and the indentor, the movement being in a same direction as the other of the sample and the indentor when the sample approaches the indentor and a distance between the sample and the indentor is within a predetermined distance.

6. The hardness testing apparatus according to claim 1, further comprising:

an impression forming mechanism for forming an impression on a surface of a sample with an indentor, the impression forming mechanism having an impact reducing unit for controlling a movement of one of the sample and the indentor, the movement being in a same direction as the other of the sample and the indentor when the sample approaches the indentor and a distance between the sample and the indentor is within a predetermined distance.

7. A hardness testing method employed by a hardness testing apparatus having a sample table for mounting a sample thereon and an electromagnetic brake for controlling an elevating operation of the sample table, the method comprising:

supplying a current to the electromagnetic brake and inverting a direction of the current supplied to the electromagnetic brake at a predetermined timing.

8. The hardness testing method according to claim 7, wherein the current supplying step supplies a driving current to drive the electromagnetic brake and then supplies a current, which has an opposite direction to the driving current, in a shorter time than the driving current.

9. The hardness testing method according to claim 8, wherein the current supplying step supplies the driving current to the electromagnetic brake in an opposite direction of the prior driving current, which was supplied to the electromagnetic brake, every time when the electromagnetic brake is driven.

10. The hardness testing method according to claim 7, further comprising:

applying a high-frequency voltage to the electromagnetic brake in order to demagnetize the sample table that is magnetized by the electromagnetic brake.

* * * * *